US00PP11866P2

(12) United States Plant Patent
Moser

(10) Patent No.: US PP11,866 P2
(45) Date of Patent: May 8, 2001

(54) CHRYSANTHEMUM PLANT NAMED 'TEMPTRESS'

(75) Inventor: Frank Moser, Alva, FL (US)

(73) Assignee: Mozant LLC, Oxnard, CA (US)

( * ) Notice: Subject to any disclaimer, the term of this patent is extended or adjusted under 35 U.S.C. 154(b) by 0 days.

(21) Appl. No.: 09/243,748

(22) Filed: Feb. 3, 1999

(51) Int. Cl.[7] ..... A01H 5/00
(52) U.S. Cl. ..... Plt./286
(58) Field of Search ..... Plt./286, 297, 298

*Primary Examiner*—Howard J. Locker
(74) *Attorney, Agent, or Firm*—Christie, Parker & Hale, LLP

(57) ABSTRACT

A new plant variety of chrysanthemum producing reddish-purple daisy-type flowers with many ray florets and a small yellow disc.

1 Drawing Sheet

BACKGROUND OF THE INVENTION

The present invention is directed to a new and distinct variety of chrysanthemum botanically classified as *Dendranthema morifolium*. The varietal denomination of the new chrysanthemum is 'Temptress'.

The female parent of the new variety is an undistributed seedling identified as 96-351-056 and the male parent is an undistributed seedling identified as 94-11-099. The new variety has been asexually reproduced by vegetative cuttings in Ventura County, Calif. and the distinguishing characteristics are retained through successive generations of asexual reproduction.

SUMMARY OF THE INVENTION

'Temptress' is a chrysanthemum plant variety with reddish-purple daisy-type flowers with many ray florets and a small yellow disc.

BRIEF DESCRIPTION OF ILLUSTRATION

The accompanying photographs shows typical specimens of the plant and flowers of the new variety with colors being as nearly true as possible with an illustration of this type.

DESCRIPTION OF THE PLANT

The following description of the new variety is of specimens grown in a greenhouse in Ventura County, Calif. in the month of April. 'Temptress' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'Temptress' is about 29 days and a response time of about 6.5 weeks. As recognized in the trade, the term "shelf life" refers to the length of time before blooms become completely dry on the plant. No treatment with growth retardant was used with plants described. Useful growing conditions include night temperatures of about 62°–65° F., day temperatures of about 70°–75° F. The new variety is naturally blooming about September 10 in Ventura County, Calif.

Plant:
- *Habit.*—Herbaceous perennial mounding plant form.
- *Height.*—About 26 cm.
- *Number of breaks from pinch.*—About 4 to 5.
- *Length of lateral branches.*—About 22 cm.
- *Stem color.*—Near 138A.

Foliage:
- *Leaf arrangement.*—Alternate.
- *Number of leaves per lateral branch.*—About 14 fully expanded leaves.
- *Leaf size.*—Length: About 6.5 cm. Width: About 3.4 cm.
- *Leaf shape.*—Ovate.
- *Attachment.*—Petioled.
- *Leaf apex.*—Acute.
- *Base.*—Tapered.
- *Margin.*—Palmately lobed.
- *Aspect.*—Slightly convex.
- *Surface.*—Top: Lightly pubescent. Bottom: Pubescent.
- *Venation.*—Prominent on underside. Color: Underside: Near 147C. Upper side: Near 146C.
- *Petiole.*—Length: About 1.7 cm. Color: Near 147C.

Color:
- *Mature leaf.*—Top: Near 137A. Bottom: Near 137C.
- *Young leaf.*—Top: Near 137B. Bottom: Near 137C.

Bloom:
- *Inflorescence form.*—Cyme.
- *Flower form.*—Daisy-type.
- *Number of blooms per branch.*—About 10.
- *Diameter of fully expanded bloom.*—4.5 cm.
- *Diameter of disc.*—1.1 cm.
- *Depth of fully expanded bloom.*—About 1.8 cm.
- *Sepal number.*—About 25. Color: Near 137A.
- *Peduncle.*—Length: The terminal peduncle is shortest, with the length gradually increasing down the stem. Average terminal peduncle length is about 3 cm, average lower lateral peduncle length is about 7 cm. Habit: Straight. Surface: Pubescent. Color: Near 138A.
- *Flower bud* (*when just showing color*).—Color: Near 58A. Diameter: About 0.9 cm. Height: About 1 cm.
- *Ray florets.*—Number per flower: About 110. Texture: Matte. Shape: Oblanceolate. Apex: 3 obtuse lobes. Base: Tapered. Margin: Entire. Aspect: Concave. Length: About 2 cm. Width: about 0.5 cm.

*Disc florets.*—Number per flower: About 55. Texture. Shiny. Shape: Cylindric. Length: About 0.6 cm. Width: About 0.1 cm.

*Fragrance.*—Very slight.

Flower color:

*General flower description.*—Reddish-purple daisy-type with a yellow eye.

*Ray florets, top side.*—Immature: Near 58A. Mature: Near 53D. Fading: Near 59C.

*Ray floret, under side.*—Immature: Near 63A. Mature: Near 63B. Fading: Near 70C.

*Disc florets.*—Immature: Near 6C. Mature: Near 13B. Fading: Near 13C.

*Changes as the flower ages.*—Color fades slightly. Flower shape is retained, ray floret color fades slightly, both ray florets and disc florets are persistent on the plant.

Reproductive organ:

*Ray florets.*—Pistillate. Stigma shape: 2 branched. Stigma color: Near 6C. Style length: About 0.4 cm. Style color: Near 3D.

*Disc florets.*—Stigma shape; 2 branched. Stigma color: Near 2B. Style length: About 0.5 cm. Style color: Near 2D. Stamen number: About 5. Anther length: About 0.2 cm. Pollen color: Near 15A. Pollen quantity: Moderate.

What is claimed is:

1. A new and distinct chrysanthemum plant of the variety substantially as herein shown and described.

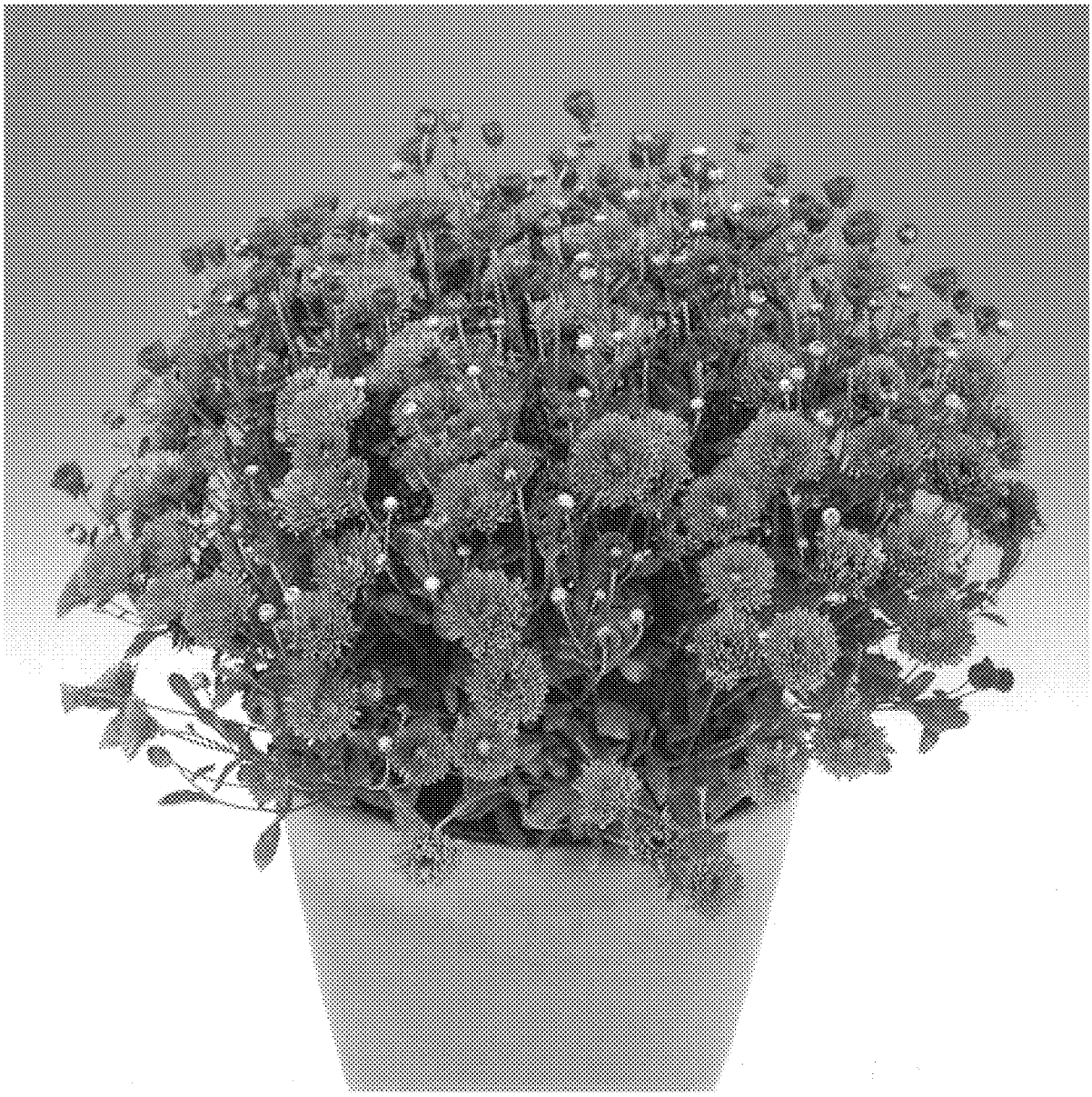

* * * * *